United States Patent [19]

Buzzetti et al.

[11] Patent Number: 5,488,057
[45] Date of Patent: Jan. 30, 1996

[54] 2-OXINDOLE COMPOUNDS WHICH HAVE USEFUL TYROSINE KINASE ACTIVITY

[75] Inventors: Franco Buzzetti, Monza (Milan); Antonio Longo, Milan; Maristella Colombo, Cesano Boscone (Milan), all of Italy

[73] Assignee: Farmitalia Carlo Erba S.r.l., Milan, Italy

[21] Appl. No.: 294,350

[22] Filed: Aug. 23, 1994

Related U.S. Application Data

[62] Division of Ser. No. 126,687, Sep. 27, 1993, Pat. No. 5,374,652, which is a continuation of Ser. No. 768,259, Oct. 28, 1991, abandoned.

[30] Foreign Application Priority Data

Feb. 28, 1990 [GB] United Kingdom .................. 9004483

[51] Int. Cl.$^6$ ...................... C07D 401/06; A61K 31/47; A61K 31/405

[52] U.S. Cl. ...................... 514/312; 546/141; 546/142; 546/145; 546/146; 546/147; 546/148; 546/152; 546/153; 546/155; 546/157; 546/158; 546/174; 546/176; 546/177; 546/178; 546/179; 546/180; 548/458; 514/314; 514/307; 514/309; 514/415; 514/418; 514/419

[58] Field of Search ...................... 546/141, 142, 546/145, 146, 147, 148, 152, 153, 155, 157, 158, 174, 176, 177, 178, 179, 180; 548/458; 514/307, 309, 312, 314, 415, 418, 419

[56] References Cited

U.S. PATENT DOCUMENTS 5,122,537  6/1992  Buzzetti et al. .................. 514/510
5,130,472  7/1992  Buzzetti et al. .................. 560/252

OTHER PUBLICATIONS

Hodges et al, Canadian Journal of Chemistry, vol. 46, No. 13, Jul. 1, 1968, pp. 2189–2194.
von Sobneck et al, Chem. Ber, vol. 102 (4), (1969) pp. 1347–1356.
Il Farmaco 48 (5), 615–636 (1993) by Buzzetti F. et al.

*Primary Examiner*—C. Warren Ivy
*Assistant Examiner*—Zinna N. Davis
*Attorney, Agent, or Firm*—Oblon, Spivak, McClelland, Maier & Neustadt

[57] ABSTRACT

The present invention provides novel aryl- and heteroarylethenylene derivatives which are useful as tyrosine kinase activity inhibitors.

6 Claims, No Drawings

2-OXINDOLE COMPOUNDS WHICH HAVE USEFUL TYROSINE KINASE ACTIVITY

This is a division of application Ser. No. 08/126,687, filed on Sep. 27, 1993, now U.S. Pat. No. 5,374,652 which is a continuation of Ser. No. 07/768,259 filed Oct. 28, 1991 (now abandoned).

The present invention relates to new aryl- and heteroaryl-ethenylene derivatives, to a process for their preparation, to pharmaceutical compositions containing them and to their use as therapeutic agents.

The present invention provides compounds having the following general formula (I)

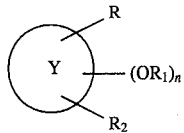

(I)

wherein
Y is a mono- or bicyclic ring system chosen from (A), (B), (C), (D), (E), (F) and (G)

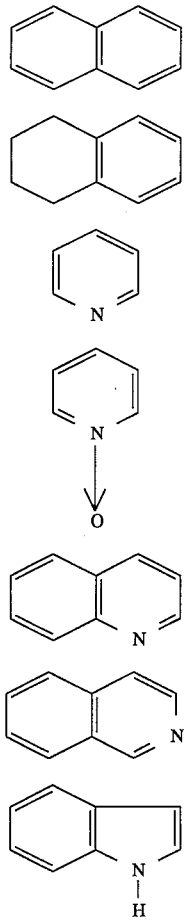

R is a group of formula (a), (b), (c), (d), (e), (f), (g), (h), (i) or (j)

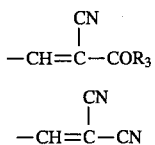

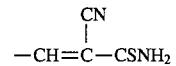

(c)

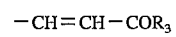

(d)

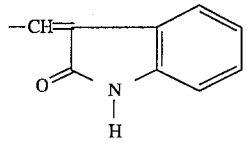

(e)

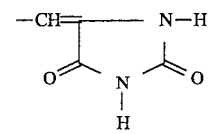

(f)

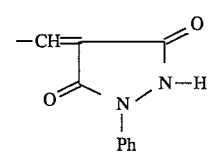

(g)

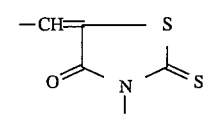

(h)

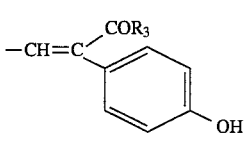

(i)

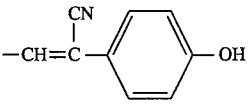

(j)

in which $R_3$ is —OH or —NH$_2$ and Ph means phenyl; $R_1$ is hydrogen, $C_1$–$C_6$ alkyl or $C_2$–$C_6$ alkanoyl; $R_2$ is hydrogen, halogen, cyano or $C_1$–$C_6$ alkyl; n is zero or an integer of 1 to 3: n is zero or an integer of 1 to 3 when Y is a ring system (A); it is zero, 1 or 2 when Y is a ring system (B), (E), (F) or (G); or it is zero or 1 when Y is a ring system (C) or (D); and the pharmaceutically acceptable salts thereof; and wherein each of the substituents R, OR$_1$ and R$_2$ may be independently on either of the aryl or heteroaryl moieties of the bicyclic ring system (A), (E), (F) and (G), whereas only the benzene moiety may be substituted in the bicyclic ring system (B).

The invention includes within its scope all the possible isomers, stereoisomers, in particular Z and E isomers and their mixtures, and the metabolites and the metabolic precursors or bio-precursors (otherwise known as pro-drugs) of the compounds of formula (I).

The substituent R is preferably linked to position 1 or 2 in ring system (A) and (B), to position 4 in ring system (C) and (D), to position 5 or 8 in ring system (E) and (F) and to position 3 or 7 in ring system (G). The substituent $R_2$ may be independently on either of the rings in the bicyclic ring systems (A), (B), (E), (F) and (G).

When Y is a bicyclic ring system as defined under (A), (E) or (F) the —OR$_1$ groups are preferably on the same benzene moiety as the R group. In any of ring systems (A) to (G), the substituent $R_2$ is preferably located on the same 6-membered ring as the substituent —OR$_1$ in the ortho-, meta- or para-position with respect to —OR$_1$. Preferably $R_2$ is located in a position ortho- or para- to —OR$_1$.

A substituent —OR$_1$ is preferably linked to position 1, 2, 3, 4, 5 or 8, in particular to position 1, 2, 3 or 4, in ring systems (A) and (B). A substituent —OR$_1$ is preferably linked to position 2, 3, 4 or 5, in particular to position 3, 4 or 5, in ring systems (C) and (D). A substituent —OR$_1$ is preferably linked to position 3, 4, 5, 6, 7 or 8, in particular to position 5, 6, 7 or 8, in ring system (E) and (F). A substituent —OR$_1$ is preferably linked to position 3, 4, 5, 6 or 7, in particular to position 4, 5, 6 or 7 in ring system (G). Of course only one of the substituents R, —OR$_1$ and R$_2$ can be linked to the same position in ring systems (A) to (G).

When n is 2 or 3, the —OR$_1$ groups may be the same or different.

The alkyl groups, and the alkyl moiety in the alkanoyl groups, may be a branched or straight alkyl chain. A $C_1$–$C_6$ alkyl group is preferably a $C_1$–$C_4$ alkyl group, e.g. methyl, ethyl, propyl, isopropyl, butyl, sec-butyl or tert-butyl, in particular methyl or ethyl. A $C_2$–$C_6$ alkanoyl group is preferably a $C_2$–$C_4$ alkanoyl group, in particular acetyl, propionyl or butyryl.

A halogen is, preferably, chlorine, bromine or fluorine, in particular bromine.

Pharmaceutically acceptable salts of the compounds of the invention include acid addition salts, with inorganic, e.g. nitric, hydrochloric, hydrobromic, sulphuric, perchloric and phosphoric acids, or organic, e.g. acetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium, bases or alkaline-earth metal, especially calcium or magnesium bases, or with organic bases, e.g. alkylamines, preferably triethyl-amine.

As stated above the present invention also includes within its scope pharmaceutically acceptable bio-precursors (otherwise known as pro-drugs) of the compounds of formula (I), i.e. compounds which have a different formula to formula (I) above but which nevertheless upon administration to a human being are converted directly or indirectly in vivo into a compound of formula (I). Preferred compounds of the invention are the compounds of formula (I), wherein Y is a monocyclic or bicyclic ring system chosen from (A) to (G), as defined above;

R is a group of formula (a), (b), (c), (d), (e), (i) or (j) as defined above;

R$_1$ is hydrogen, $C_1$–$C_4$ alkyl or $C_2$–$C_4$ alkanoyl;

R$_2$ is hydrogen;

n is a defined above; and the pharmaceutically acceptable salts thereof.

More preferred compounds of the invention are the compounds of formula (I), wherein Y is a bicyclic ring system of formula (A), (B) or (E), as defined above;

R is a group of formula (a), (d), (e), (i) or (j), as defined above;

R$_1$ and R2 are hydrogen;

n is zero or 1; and the pharmaceutically acceptable salts thereof.

Examples of specific compounds of the invention are the following compounds which, when appropriate, may be either Z- or E- diastereomers or Z, E- mixtures of said diastereomers:

2-cyano-3-(2-hydroxynaphth-1-yl)acrylamide;
2-cyano-3-(3-hydroxynaphth-1-yl)acrylamide;
2-cyano-3-(4-hydroxynaphth-1-yl)acrylamide;
2-cyano-3-(1-hydroxynaphth-2-yl)acrylamide;
2-cyano-3-(3-hydroxynaphth-2-yl)acrylamide;
2-cyano-3-(4-hydroxynaphth-2-yl)acrylamide;
2-cyano-3-(2-hydroxynaphth-1-yl)acrylic acid;
2-cyano-3-(3-hydroxynaphth-1-yl)acrylic acid;
2-cyano-3-(4-hydroxynaphth-1-yl)acrylic acid;
2-cyano-3-(1-hydroxynaphth-2-yl)acrylic acid;
2-cyano-3-(3-hydroxynaphth-2-yl)acrylic acid;
2-cyano-3-(4-hydroxynaphth-2-yl)acrylic acid;
2-cyano-3-(2-hydroxynaphth-1-yl)thioacrylamide;
2-cyano-3-(3-hydroxynaphth-1-yl)thioacrylamide;
2-cyano-3-(4-hydroxynaphth-1-yl)thioacrylamide;
2-cyano-3-(1-hydroxynaphth-2-yl)thioacrylamide;
2-cyano-3-(3-hydroxynaphth-2-yl)thioacrylamide;
2-cyano-3-(4-hydroxynaphth-2-yl)thioacrylamide;
2-(4-hydroxyphenyl)-3-(naphth-1-yl)acrylamide;
2-(4-hydroxyphenyl)-3-(naphth-2-yl)acrylamide;
2-(4-hydroxyphenyl)-3-(naphth-1-yl)acrylic acid;
2-(4-hydroxyphenyl)-3-(naphth-2-yl)acrylic acid;
2-cyano-3-(2-hydroxy-5,6,7,8-tetrahydronaphth-1-yl)acrylamide;
2-cyano-3-(3-hydroxy-5,6,7,8-tetrahydronaphth-1-yl)acrylamide;
2-cyano-3-(4-hydroxy-5,6,7,8-tetrahydronaphth-1-yl)acrylamide;
2-cyano-3-(1-hydroxy-5,6,7,8-tetrahydronaphth-2-yl)acrylamide;
2-cyano-3-(3-hydroxy-5,6,7,8-tetrahydronaphth-2-yl)acrylamide;
2-cyano-3-(4-hydroxy-5,6,7,8-tetrahydronaphth-2-yl)acrylamide;
2-cyano-3-(2-hydroxy-5,6,7,8-tetrahydronaphth-1-yl)acrylic acid;
2-cyano-3-(3-hydroxy-5,6,7,8-tetrahydronaphth-1-yl)acrylic acid;
2-cyano-3-(4-hydroxy-5,6,7,8-tetrahydronaphth-1-yl)acrylic acid;
2-cyano-3-(1-hydroxy-5,6,7,8-tetrahydronaphth-2-yl)acrylic acid;
2-cyano-3-(3-hydroxy-5,6,7,8-tetrahydronaphth-2-yl)acrylic acid;
2-cyano-3-(4-hydroxy-5,6,7,8-tetrahydronaphth-2-yl)acrylic acid
2-cyano-3-(2-hydroxy-5,6,7,8-tetrahydronaphth-1-yl)thioacrylamide;
2-cyano-3-(3-hydroxy-5,6,7,8-tetrahydronaphth-1-yl)thioacrylamide;
2-cyano-3-(4-hydroxy-5,6,7,8-tetrahydronaphth-1-yl)thioacrylamide;
2-cyano-3-(1-hydroxy-5,6,7,8-tetrahydronaphth-2-yl)thioacrylamide;
2-cyano-3-(3-hydroxy-5,6,7,8-tetrahydronaphth-2-yl)thioacrylamide;
2-cyano-3-(3-hydroxy-5,6,7,8-tetrahydronaphth-2-yl)thioacrylamide;
2-(4-hydroxyphenyl)-3-(5,6,7,8-tetrahydronaphth-1-yl)acrylamide;
2-(4-hydroxyphenyl)-3-(5,6,7,8-tetrahydronaphth-2-yl)acrylamide;
2-(4-hydroxyphenyl)-3-(5,6,7,8-tetrahydronaphth-1-yl)acrylic acid;
2-(4-hydroxyphenyl)-3-(5,6,7,8-tetrahydronaphth-2-yl)acrylic acid;
2-cyano-3-(3-hydroxyquinolin-2-yl)acrylamide;
2-cyano-3-(4-hydroxyquinolin-2-yl)acrylamide;
2-cyano-3-(2-hydroxyquinolin-3-yl)acrylamide;
2-cyano-3-(4-hydroxyquinolin-3-yl)acrylamide;
2-cyano-3-(2-hydroxyquinolin-4-yl)acrylamide;
2-cyano-3-(3-hydroxyquinolin-4-yl)acrylamide;
2-cyano-3-(3-hydroxyquinolin-2-yl)acrylic acid;

2-cyano-3-(4-hydroxyquinolin-2-yl)acrylic acid;
2-cyano-3-(2-hydroxyquinolin-3-yl)acrylic acid;
2-cyano-3-(4-hydroxyquinolin-3-yl)acrylic acid;
2-cyano-3-(2-hydroxyquinolin-4-yl)acrylic acid;
2-cyano-3-(3-hydroxyquinolin-4-yl)acrylic acid;
2-cyano-3-(3-hydroxyquinolin-2-yl)thioacrylamide
2-cyano-3-(4-hydroxyquinolin-2-yl)thioacrylamide
2-cyano-3-(2-hydroxyquinolin-3-yl)thioacrylamide
2-cyano-3-(4-hydroxyquinolin-3-yl)thioacrylamide
2-cyano-3-(2-hydroxyquinolin-4-yl)thioacrylamide
2-cyano-3-(3-hydroxyquinolin-4-yl)thioacrylamide
2-(4-hydroxyphenyl)-3-(quinolin-2-yl)acrylamide
2-(4-hydroxyphenyl)-3-(quinolin-3-yl)acrylamide;
2-(4-hydroxyphenyl)-3-(quinolin-4-yl)acrylamide;
2-(4-hydroxyphenyl)-3-(quinolin-2-yl)acrylic acid;
2-(4-hydroxyphenyl)-3-(quinolin-3-yl)acrylic acid;
2-(4-hydroxyphenyl)-3-(quinolin-4-yl)acrylic acid;
3-[(3-hydroxy-1-naphthyl)methylene]-2-oxindole;
3-[(4-hydroxy-1-naphthyl)methylene]-2-oxindole;
3-[(1-hydroxy-2-naphthyl)methylene]-2-oxindole;
3-[(4-hydroxy-2-naphthyl)methylene]-2-oxindole;
3-[(3-hydroxy-5,6,7,8-tetrahydronaphth-1-yl)methylene]-2-oxindole;
3-[(4-hydroxy-5,6,7,8-tetrahydronaphth-1-yl)methylene]-2-oxindole;
3-[(1-hydroxy-5,6,7,8-tetrahydronaphth-2-yl)methylene]-2-oxindole;
3-[(4-hydroxy-5,6,7,8-tetrahydronaphth-2-yl)methylene]-2-oxindole;
3-[(7-hydroxyquinolin-5-yl)methylene]-2-oxindole;
3-[(8-hydroxyquinolin-5-yl)methylene]-2-oxindole;
3-[(7-hydroxyquinolin-6-yl)methylene]-2-oxindole;
3-[(8-hydroxyquinolin-6-yl)methylene]-2-oxindole,
and, if the case, the pharmaceutically acceptable salts thereof.

The compounds of the invention, and the pharmaceutically acceptable salts thereof, can be obtained by a process comprising the condensation of an aldehyde of formula (II)

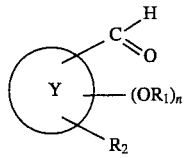

wherein
Y, $R_1$, $R_2$ and n are as defined above with a compound of formula (a'), (b'), (c'), (d'), (e'), (f'), (g'), (h'), (i') or (j'), respectively,

| | |
|---|---|
| $NC-CH_2-COR_3$ | (a') |
| $NC-CH_2-CN$ | (b') |
| $NC-CH_2-CSNH_2$ | (c') |
| $HOOC-CH_2-COR_3$ | (d') |

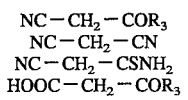 (e')

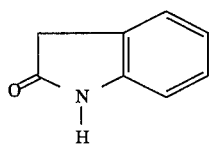 (f')

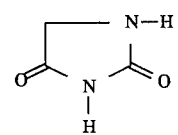

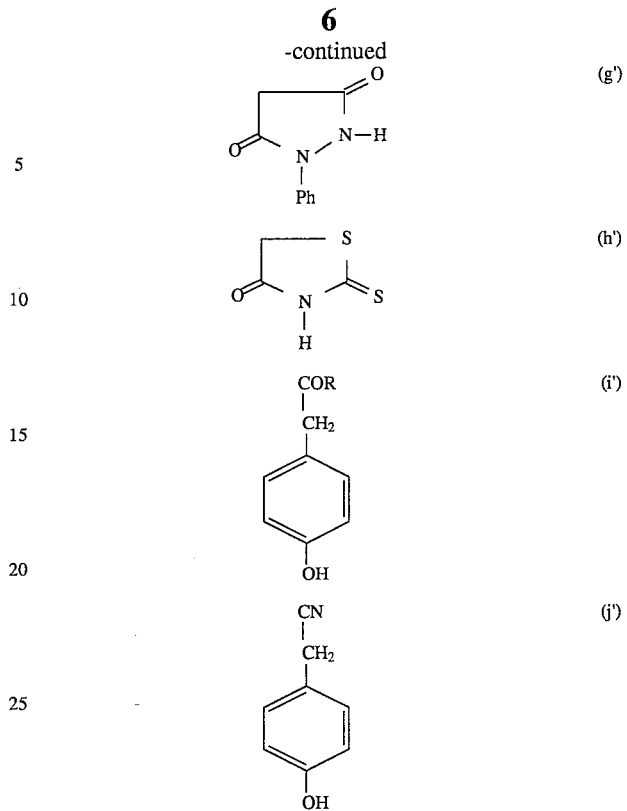

wherein $R_3$ and Ph are as defined above; and if desired, converting a compound of formula (I) into another compound of formula (I), and/or, if desired, converting a compound of formula (I) into a pharmaceutically acceptable salt thereof, and/or, if desired, converting a salt into a free compound, and/or, if desired, separating a mixture of isomers of a compound of formula (I) into the single isomers.

The reaction of a compound of formula (II) with a compound of formula (a'), (b'), (c'), (d'), (e'), (f'), (g'), (h'), (i') or (j'), is an analogy process which can be carried out according to known methods, as herebelow described; preferably in the presence of a basic catalyst, e.g. pyridine, piperidine, dimethylmine, or a suitable alkali metal hydroxide or alkoxide.

For example the reaction of a compound of formula (II) with a compound of formula (a'), (b'), (c'), (e'), (f'), (g') or (h'), respectively, may be carried out under the conditions of the Knoevenagel reactions as described e.g. by G. Jones in Organic Reactions 15, 204 (1967). Suitable catalyst are organic bases such as pyridine, piperidine or diethylamine. The condensation may be performed in an inert organic solvent e.g. pyridine, ethanol, methanol, benzene or dioxane at temperature ranging from about 0° C. to about 100° C. Preferably the reaction is carried out in warm ethanol solution in the presence of piperidine catalyst.

The reaction of a compound of formula (II) with a compound of formula (d') may be carried out according to the Knoevenagel method as described above but using special conditions. Especially higher reaction temperatures are used in consideration of the fact that during the condensation also a decarboxylation occurs. For instance the condensation may be performed in an organic base such as pyridine (which at same time is solvent and catalyst) at temperatures ranging from about 50° to about 140° C.

The reaction of a compound of formula (II) with a compound of formula (i') may be carried out as described by R. E. Buckles et al. in J. Am. Chem. Soc. 73, 4972 (1951). According to this method equimolar amounts of the aromatic aldehyde and the phenylacetic derivative are reacted in 3–5 molequivalents of acetic anhydride in the presence of about 1 molequivalent triethylamine at temperatures ranging from about 100° to about 140° C. .

The condensation of a compound of formula (II) with a compound of formula (j') may be carried out in alcoholic solution using a metal alkoxide, e.g. sodium ethoxide, potassium t-butoxide, or a metal hydroxide, e.g. sodium hydroxide, as catalyst; at temperatures ranging from about 0° C. to about 100° C. Preferably equimolar amounts of reactants are condensed in ethanol solution at room temperature in the presence of sodium ethoxide using about 1 molequivalent for each acidic hydrogen of the latter.

A compound of formula (I) can be converted into another compound of formula (I) according to known methods. For example the de-etherification of a compound of formula (I), wherein one or more $R_1$ substituents are $C_1$–$C_6$ alkyl, so as to obtain a compound of formula (I) wherein one or more $R_1$ substituents are hydrogen may be performed by well known methods in organic chemistry. In the case of a phenolic methyl ether the cleavage can be carried out for example with boron tribromide as described by J. F. N. McOmie in Tetrahedron 24, 2289 (1968). It is advisable to use about 1 mole of boron tribromide for each ether group together with an extra mol of reagent for each group containing a potentially basic nitrogen or oxygen. The reaction may be performed in an inert organic solvent such as methylene chloride, pentane or benzene under an inert, e.g. nitrogen, atmosphere at temperatures ranging from about –78° C. to about room temperature. The acylation of a compound of formula (I) wherein one or more $R_1$ substituent is hydrogen, so as to obtain a corresponding compound of formula (I) wherein one or more $R_1$ substituent is a $C_2$–$C_6$ alkanoyl group, may be obtained by reaction with a reactive derivative of a suitable carboxylic acid, such as an anhydride or halide, in the presence of a basic agent, at temperatures ranging from about 0° C. to about 50° C. Preferably the acylation is carried out by reaction with the respective anhydride in the presence of an organic base, such as pyridine. Analogously the conversion of a compound of formula (I), wherein R is a group of formula

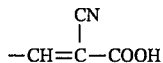

or —CH=CH—COOH, into another compound of formula (I) wherein R is a group of formula

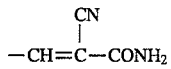

or —CH=CH—CONH$_2$, respectively, may be carried out according to known methods. For example a reactive derivative of the carboxylic acid, e.g. a suitable halide, preferably the chloride, can be reacted with aqueous ammonium hydroxide solution at a temperature ranging from about 5° C. to about 40° C.

The optional salification of a compound of formula (I) as well as the conversion of a salt into the free compound and the separation of a mixture of isomers into the single isomers may be carried out by conventional methods.

For example the separation of a mixture of geometric isomers, e.g. cis- and trans-isomers, may be carried out by fractional crystallization from a suitable solvent or by chromatography, either column chromatography or high pressure liquid chromatography.

The compounds of formula (II) may be obtained according to known methods from compounds of formula (III).

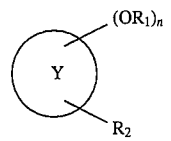

wherein Y, $R_1$, $R_2$ and n are as defined above.

For example the phenolic compound of formula (III) may be treated with chloroform and alkali hydroxides in an aqueous or aqueous alcoholic solution according, to the well known method of Reimer-Tiemann. If the starting material is an aromatic methylether the method described by N. S. Narasimhan et al. in Tetrahedron 31, 1005 (1975) can be applied. Accordingly the methylether of formula (III) is lithiated with butyl lithium in refluxing ether. Treatment of the organometallic compound with N-methylformanilide furnishes the formyl derivative. The compounds of formula (III) are known or may be obtained by known methods from known compounds.

PHARMACOLOGY

The compounds of the present invention possess specific tyrosine kinase inhibiting activity. Hence they can be useful in the treatment of cancer and other pathological proliferative conditions.

Recent studies on the molecular basis of neoplastic transformation have identified a family of genes, designed oncogenes, whose aberrant expression causes tumorigenesis.

For example, the RNA tumor viruses possess such an oncogene sequence whose expression determines neoplastic conversion of infected cells. Several of their oncogene-encoded proteins, such as pp60$^{v\text{-}src}$, p70$^{gag\text{-}yes}$, p130$^{gag\text{-}fps}$ and p70$^{gag\text{-}fgr}$ display protein tyrosine kinase activity, that is they catalyse the transfer of the δ-phosphate from adenosine triphosphate (ATP) to tyrosine residues in protein substrate. In normal cells, several growth factor receptors, for example the receptors for PDGF, EGF, δ-TGF and insulin, display tyrosine kinase activity. Binding of the growth factor (GF) activates the receptor tyrosine kinase to undergo autophosphorylation and to phosphorylate closely adjacent molecules on tyrosine.

Therefore, it is thought that the phosphorylation of these tyrosine kinase receptors plays an important role in signal transduction and that the principal function of tyrosine kinase activity in normal cells is to regulate cell growth. Perturbation of this activity by oncogenic tyresine kinase that are either overproduced and/or display altered substrate specificity may cause loss of growth control and/or neoplastic transformation. Accordingly, a specific inhibitor of tyrosine kinases can be useful in investigating the mechanism of carcinogenesis, cell proliferation and differentiation and it can be effective in prevention and chemotherapy of cancer and in other pathological proliferative conditions. The tyrosine specific protein kinase activity of these compounds is shown, e.g., by the fact that they are active in the in vitro test described by B. Ferguson et al., in J. Biol. Chem. 1985, 260, 3652.

The enzyme used is the Abelson tyrosine kinase p60$^{v\text{-}abl}$. Its production and isolation is performed according to a modification of the method of B. Ferguson etal. (ibidem). As substrate δ-casein or (Val$^5$)-angiotensin is used. The inhibitor is proincubated with the enzyme for 5 min at 25° C. The reaction conditions are:

100 mM MOPS buffer, 10 mM MgCl$_2$, 2 μM (δ-$^{32}$P) ATP (6 Ci/mmol), 1 mg/ml δ-casein [an alternative substrate is (Val$^5$) angiotensin II] and 7.5 µg/ml of enzyme in a total volume of 30 µl and pH 7.0.

The reaction is incubated for 10 min at 25° C.

Trichloroacetic acid precipitation of protein is followed by rapid filtration and quantification of phosphorylated substrate by a liquid scintillation counter. Alternatively the reaction mixture is subjected to sodium dodecyl sulfate—polyacrylamide electrophoresis and the phosphorylated substrate measured by autoradiography or P$^{32}$-counting of the excised spot.

In view of their high activity and low toxicity, the compounds of the invention can be used safely in medicine.

For example, the approximate acute toxicity (LD$_{50}$) of the compounds of the invention in the mouse, determined by single administration of increasing doses and measured on the seventh day after the treatment was found to be negligible.

The compounds of the invention can be administered in a variety of dosage forms, e.g. orally, in the form of tablets, capsules, sugar of film coated tablets, liquid solutions or suspensions; rectally, in the form of suppositories; parenterally, e.g. intramuscularly, or by intravenous injection of infusion; or topically.

The dosage depends on the age, weight, conditions of the patient and administration route; for example the dosage adopted for oral administration to adult humans may range from about 10 to about 150–200 mg pro dose, from 1 to 5 times daily.

Of course, these dosage regimens may be adjusted to provide The optimal therapeutic response.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting sugar-coating or film-coating processes.

The liquid dispersion for oral administration may be e.g. syrups, emulsions and suspensions.

The syrup may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose or polevinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusion may contain as carrier, for example, sterile water or, preferably, they may be in the form of sterile, aqueous, isotonic saline solutions.

The suppositories may contain together with the active compound a pharmaceutically acceptable carrier, e.g. cocoabutter, polyethylene glycol, a polyoxyethylene sorbitan fatty acid ester surfactant or lecithin.

Compositions for topical application e.g., creams, lotions or pastes, can be prepared by admixing the active ingredient with a conventional oleaginous or emulsifying excipient. The following examples illustrate but do not limit the invention.

EXAMPLE 1

2-cyano-3-(8-hydroxyquinolin-5-yl) acrylamide [I, Y=E, R=a, R$_1$=R$_2$=H, n=1, R$_3$=NH$_2$]

A solution of 5-formyl-8-hydroxyquinoline (173 mg, 1 mmol), cyanoacetamide (92 mg; 1.1 mmol) and piperidine (60 mg, 0.7 mmol) in absolute ethanol (20 ml) is heated for 4 h at 50° C. The reaction mixture is chilled to 0°–5° C., the precipitate filtered, the residue washed with ice-cooled ethanol and then dried under vacuum.

Pure title compound is so obtained in 70% yield (167 mg). Compounds of higher purity are obtained by crystallization from ethanol, m.p. 275°.

C$_{13}$H$_9$N$_3$O$_2$ requires: C 65.27 H 3.79 N 17.56 found: C 65.15 H 3.65 N 17.49

MS m/z: 239

IR cm (KBT) : 3100–3600 (NH,OH), 2200 (CN), 1690 (CONH$_2$), 1610, 1590, 1560, 1510 (C=C)

According to the above described procedure the following compounds can be prepared:

2-cyano-3-(2-hydroxynaphth-1-yl)acrylamide;
2-cyano-3-(3-hydroxynaphth-1-yl)acrylamide;
2-cyano-3-(4-hydroxynaphth-1-yl)acrylamide;
2-cyano-3-(1-hydroxynaphth-2-yl)acrylamide;
2-cyano-3-(3-hydroxynaphth-2-yl)acrylamide;
2-cyano-3-(4-hydroxynaphth-2-yl)acrylamide;
2-cyano-3-(2-hydroxy-5,6,7,8-tetrahydronaphth-1-yl)acrylamide;
2-cyano-3-(3-hydroxy-5,6,7,8-tetrahydronaphth-1-yl)acrylamide;
2-cyano-3-(4-hydroxy-5,6,7,8-tetrahydronaphth-1-yl)acrylamide;
2-cyano-3-(1-hydroxy-5,6,7,8-tetrahydronaphth-2-yl)acrylamide
2-cyano-3-(3-hydroxy-5,6,7,8-tetrahydronaphth-2-yl)acrylamide;
2-cyano-3-(4-hydroxy-5,6,7,8-tetrahydronaphth-2-yl)acrylamide;
2-cyano-3-(3-hydroxyquinolin-2-yl)acrylamide;
2-cyano-3-(4-hydroxyquinolin-2-yl)acrylamide;
2-cyano-3-(2-hydroxyquinolin-3-yl)acrylamide;
2-cyano-3-(4-hydroxyquinolin-3-yl)acrylamide;
2-cyano-3-(2-hydroxyquinolin-4-yl)acrylamide;
2-cyano-3-(3-hydroxyquinolin-4-yl)acrylamide;
3-[(1-naphthyl)methylene]-2-oxindole;
3-[(2-hydroxy-1-naphthyl)methylene]-2-oxindole;
3-[(3-hydroxy-1-naphthyl)methylene]-2-oxindole;
3-[(4-hydroxy-1-naphthyl)methylene]-2-oxindole;
3-[(2-naththyl)methylene]-2-oxindole;
3-[(1-hydroxy-2-naphthyl)methylene]-2-oxindole;
3-[(3-hydroxy-2-naphthyl)methylene]-2-oxindole;
3-[(4-hydroxy-2-naphthyl)methylene]-2-oxindole;

3-[5,6,7,8-tetrahydromaphth-1-yl)methylene]-2-oxindole;
3-[(2-hydroxy-5,6,7,8-tetrahydronaphth-1-yl)methylene]-2-oxindole;
3-[(3-hydroxy-5,6,7,8-tetrahydronaphth-1-yl)methylene]-2-oxindole;
3-[(4-hydroxy-5,6,7,8-tetrahydroraphth-1-yl)methylene]-2-oxindole;
3-[(5,6,7,8-tetrahydronaphth-2-yl)methylene]-2-oxindole;
3-[(1-hydroxy-5,6,7,8-tetrahydronaphth-2-yl)methylene]-2-oxindole;
3-[(3-hydroxy-5,6,7,8-tetrahydronaphth-2-yl)methylene]-2-oxindole;
3-[(4-hydroxy-5,6,7,8-tetrahydronaphth-2-yl)methylene]-2-oxindole;
3-[(quinolin-5-yl)methylene]-2-oxindole;
3-[(6-hydroxyquinolin-5-yl)methylene]-2-oxindole;
3-[(7-hydroxyquinolin-5-yl)methylene]-2-oxindole;
3-[(8-hydroxyquinolin-5-yl)methylene]-2-oxindole;
3-[(quinolin-6-yl)methylene]-2-oxindole;
3-[(5-hydroxyquinolin-6-yl)methylene]-2-oxindole;
3-[(7-hydroxyquinolin-6-yl)methylene]-2-oxindole;
3-[(8-hydroxyquinolin-6-yl)methylene]-2-oxindole;
3-[(1,4-dihydroxy-5,6,7,8-tetrahydronaphth-2-yl)methylene]-2-oxindole, $C_{19}H_{17}NO_3$ requires: C 74.25 H 5.58 N 4.56 found: C 74.01 H 5.74 N 4.48

MS m/z: 307

IR cm$^{-1}$ (KBP): 3500–3100 (OH,NH), 1670 (CO), 1605 (C=C);

3-[(quinolin-2-yl)methylene]-2-oxindole, $C_{18}H_{12}N_2O$ requires: C 79.39 H 4.44 N 10.29 found: C 79.29 H 4.45 N 10.25

MS m/z: 272

IR cm$^{-1}$ (KBr): 3180 (NH), 1710 (CO), 1620–1595–1505 (C=C, C=N);

3-[(4-hydroxyquinolin-2-yl)methylene]-2-oxindole $C_{18}H_{12}N_2O_2$ requires: C 74.98 H 4.20 N 9.72 found: C 74.66 H 4.25 N 9.38

MS m/z: 288

IR cm$^{-1}$ (KBr): 3430 (OH,NH), 1675 (CO), 1630 (C=C) 1595–1580–1530–1515 (arom);

3-[(quinolin-4-yl)methylene]-2-oxindole, $C_{18}H_{12}N_2O$ requires: C 79.39 H 4.44 N 10.29;

3-[(quinolin-3-yl)methylene$_3$-2-oxindole, $C_{18}H_{12}N_2O$ requires: C 79.39 H 4.44 N 10.29 found: C 79.20 H 4.71 N 10.14

MS m/z: 272

IR cm$^{-1}$ (KBr): 3500–3100 (NH), 1695 (CO), 1620–1580–1500 (C=C, C=N);

4-[(indol-3-yl)methylene]-1-phenyl-pyrazolidin-3,5-dione, $C_{18}H_{13}N_3O_2$ requires: C 71.27 H 4.32 N 13.85 found: C 71.05 H 4.33 N 13.64

MS m/z: 303

IR cm$^{-1}$ (KBr): 3600–3100 (NH), 1705–1650 (CONH), 1600–1580–1500 (arom), and 5-[(indol-3-yl)methylene]-hydantoin, $C_{12}H_9N_3O_2$ requires: C 63.43 H 3.99 N 18.49 found: C 63.20 H 3.71 N 18.31

MS m/z: 227

IR cm$^{-1}$ (KBr) : 3600–3100 (NH), 1740–1700–1650 (CONH), 1620–1580–1530 (C=C).

EXAMPLE 2

2-cyano-3-(2-hydroxynaphth-1-yl) thioacrylamide
[I, Y=A, R=c, $R_1=R_2$=H, n=1]

A mixture of 2-hydroxy-1-naphthaldehyde (172 mg, 1 mmol), 2-cyanothioacetamide (110 mg, 1.1 mmol), N,N-diethylaminoethanol (23 mg, 0.2 mmol) and 15 ml ethanol is stirred for 30 min at reflux under nitrogen. Then the mixture is chilled, the precipitate filtered, washed with ice-cooled ethanol and dried in a vacuum-oven. Thus an almost pure title compound is obtained in 85% yield (1080 mg). Recrystallization from ethanol furnishes very pure samples.

$C_{14}H_{10}N_2OS$ requires: C 66.12 H 3.96 N 11.01 S 12.61 found: C 66.05 H 3.85 N 10.95 S 12.55

MS m/z: 254

IR cm$^{-1}$ (KBr): 3300÷2500 (NH, OH), 2020 (CN), 1640 (C-N, N-H ), 1600–1560–1510 (C=C)

According to the above described procedure the following compounds can be prepared:

2-cyano-3-(3-hydroxynaphth-1-yl)thioacrylamide;
2-cyano-3-(4-hydroxynaphth-1-yl)thioacrylamide;
2-cyano-3-(1-hydroxynaphth-2-yl)thioacrylamide;
2-cyano-3-(3-hydroxynaphth-2-yl)thioacrylamide;
2-cyano-3-(4-hydroxynaphth-2-yl)thioacrylamide;
2-cyano-3-(2-hydroxy-5,6,7,8-tetrahydronaphth-1-yl)thioacrylamide;
2-cyano-3-(3-hydroxy-5,6,7,8-tetrahydronaphth-1-yl)thioacrylamide;
2-cyano-8-(4-hydroxy-5,6,7,8-tetrahydronaphth-1-yl)thioacrylamide;
2-cyano-3-(1-hydroxy-5,6,7,8-tetrahydronaphth-2-yl)thioacrylamide;
2-cyano-3-(3-hydroxy-5,6,7,8-tetrahydronaphth-2-yl)thioacrylamide;
2-cyano-3-(4-hydroxy-5,6,7,8-tetrahydronaphth-2-yl)thioacrylamide;
2-cyano-3-(3-hydroxyquinolin-2-yl)thioacrylamide;
2-cyano-3-(4-hydroxyquinolin-2-yl)thioacrylamide;
2-cyano-3-(2-hydroxyquinolin-3-yl)thioacrylamide;
2-cyano-3-(4-hydroxyquinolin-3-yl)thioacrylamide;
2-cyano-3-(2-hydroxyquinolin-4-yl)thioacrylamide;
2-cyano-3-(4-hydroxyquinolin-4-yl)thioacrylamide, and
2-cyano-3-(8-hydroxyquinolin-5-yl)thioacrylamide, $C_{13}H_9N_3OS$ requires: C 61.16 H 3.55 N 16.46 found: C 60.99 H 3.59 N 16.26

MS m/z: 255

IR cm (KBr): 3440 (OH), 3330–3180 (NH), 2220 (CN), 1650 (NH), 1610–1570–1510 (C=C, C=N).

EXAMPLE 3

2-cyano-3-(1-hydroxynaphth-2-yl)acrylic acid [I, Y=A, R=a, $R_1=R_2$=H, $R_3$=OH, n=1]

To a mixture of 1-hydroxy-2-naphthaldehyde (172 mg, 1 mmol) and cyanoacetic acid (85 mg, 1 mmol) in dry dioxane (2 ml) piperidine (42 mg, 0.5 mmol) is added dropwise at 0°5° C. The mixture is kept overnight at room temperature. The crystals formed are filtered and recrystallized from chloroform. Thus 200 mg of pure title compound are obtained corresponding to 90% yield.

$C_{14}H_8NO_2$ requires: C 75.33 H 4.06 N 6.28 found: C 75.20 H 3.95 N 6.15

MS m/z: 223

IR cm$^{-1}$ (KBr): 3300–2500 (COOH, OH), 2200 (CN), 1690 (COOH), 1600–1560–1510 (C=C)

Following the above reported procedure and starting from the appropriate aldehyde derivative the following compounds can be prepared:

2-cyano-3-(2-hydroxynaphth-1-yl)acrylic acid;
2-cyano-3-(3-hydroxynaphth-1-yl)acrylic acid;

2-cyano-3-(4-hydroxynaphth-1-yl)acrylic acid;
2-cyano-3-(3-hydroxynaphth-2-yl)acrylic acid;
2-cyano-3-(4-hydroxynaphth-2-yl)acrylic acid;
2-cyano-3-(2-hydroxy-5,6,7,8-tetrahydronaphth-1-yl)acrylic acid;
2-cyano-3-(3-hydroxy-5,6,7,8-tetrahydronaphth-1-yl)acrylic acid;
2-cyano-3-(4-hydroxy-5,6,7,8-tetrahydronaphth-1-yl)acrylic acid;
2-cyano-3-(1-hydroxy-5,6,7,8-tetrahydronaphth-2-yl)acrylic acid;
2-cyano-3-(3-hydroxy-5,6,7,8-tetrahydronaphth-2-yl)acrylic acid;
2-cyano-3-(4-hydroxy-5,6,7,8-tetrahydronaphth-2-yl)acrylic acid;
2-cyano-3-(3-hydroxyquinolin-2-yl)acrylic acid;
2-cyano-3-(4-hydroxyquinolin-2-yl)acrylic acid;
2-cyano-3-(2-hydroxyquinolin-3-yl)acrylic acid;
2-cyano-3-(4-hydroxyquinolin-3-yl)acrylic acid;
2-cyano-3-(2-hydroxyquinolin-4-yl)acrylic acid; and
2-cyano-3-(3-hydroxyquinolin-4-yl)acrylic acid.

EXAMPLE 4

3-(1-hydroxy-5,6,7,8-tetrahydronaphth-2-yl)acrylic acid [I, Y=B, R=i, $R_1$=$R_2$=H, $R_3$=OH, n=1]

A mixture of 1-hydroxy-5,6,7,8-tetrahydro-2-naphthaldehyde (176 mg, 1 mmol), malonic acid (208 mg, 2 mmol), piperidine (85 mg, 1 mmol) and pyridine (1 ml) are heated at 100° C. for 3 h and at reflux for ½ h. The mixture is then cooled and poured onto ice and hydrochloric acid. The precipitated material is separated by filtration and then recrystallized from ethanol thus giving pure title compound in 80% yield (174 mg).

$C_{13}H_{14}O_3$ calc.: C 71.54 H 6.46 found: C 71.35 H 6.30

MS m/z: 218

IR $cm^{-1}$ (KBr): 3300–2500 (COOH, OH), 1690 (COOH), 1640 (C=C)

EXAMPLE 5

2-(4-hydroxyphenyl)-3-(napth-2-yl)acrylic acid [I, Y=A, R=i, $R_2$=H, $R_3$=OH, n=zero]

A mixture of 2-naphthaldehyde (156 mg, 1 mmol), 4-hydroxyphenylacetic acid (152 mg, 1 mmol), triethylamine (101 mg, 1 mmol) and acetic anhydride (510 mg, 5 mmol) are heated for 5 h at 100° C.

After cooling, the mixture is treated with diluted hydrochloric acid and then extracted with ethylacetate. The organic layer is separated and reextracted with diluted sodium hydroxide solution. The aqueous phase is separated and the raw product isolated by precipitation with hydrochloric acid. Pure title compound is obtained by crystallization from isopropanol in 60% yield (174 mg).

$C_{19}H_{14}O_3$ calc.: C 78.60 H 4.86 found: C 78.69 H 4.89

MS m/z: 290

IR $cm^{-1}$ (KBr): 3600–2500 (OH, COOH), 1680 (COOH), 1600, 1585, 1510 (C=C)

By proceeding analogously the following compounds can be prepared:

2-(4-hydroxyphenyl)-3-(quinolin-3-yl)acrylic acid
$C_{18}H_{13}NO_3$ calc.: C 74.21 H 4.50 N 4.81 found: C 73.85 H 4.37 N 1.53
MS m/z: 291
IR $cm^{-1}$: 3380 (OH), 3100–1800 (COOH), 1670 (COOH) 1605, 1580, 1510 (C=C)
2-(4-hydroxyphenyl)-3-(naphth-1-yl)acrylic acid;
2-(4-hydroxyphenyl)-3-(5,6,7,8-tetrahydronaphth-1-yl)acrylic acid;
2-(4-hydroxyphenyl)-3-(5,6,7,8-tetrahydronaphth-2-yl)acrylic acid;
2-(4-hydroxyphenyl)-3-(quinolin-2-yl)acrylic acid; and
2-(4-hydroxyphenyl)-3-(quinolin-4-yl)acrylic acid.

EXAMPLE 6

2-(4-hydroxyphenyl)-3-(naphth-2-yl)acrylamide [I, Y=A, R=i, $R_2$=$H_1$$R_3$=$NH_2$, n=zero]

A mixture of 2-naphthaldehyde (156 mg, 1 mmol), 4-hydroxyphenylacetic acid (152 mg, 1 mmol), triethylamine (101 mg, 1 mmol) and acetic anhydride (510 mg, 5 mmol) are heated for 5 h at 100° C. The mixture is treated with diluted hydrochloric acid after cooling and then extracted with ethylacetate. The organic layer is extracted with sodium hydroxide solution. After separation of the aqueous phase the raw carboxilic acid is isolated by precipitation with hydrochloric acid.

The raw carboxylic acid is transformed in its acid chloride by treatment with thionyl chloride (1190 mg, 10 mmol) in boiling benzene (5 ml) for 2 h. After evaporation to dryness under vacuum the raw acid chloride is transformed to the amide by reaction with diluted ammonium hydroxide at room temperature for 1 h. The raw product is obtained by filtration, washing and drying under vacuum. Crystallization from isopropanol furnishes pure title compound in 50% yield (145 mg).

$C_{19}H_{15}NO_2$ calc.: 78.87 H 5.23 N 4.84 found: C 78.71 H 5.09 N 4.65

MS m/z: 289

IR $cm^{-1}$ (KBr): 3600–3100 (OH, NH), 1650 (CONH) 1610, 1560, 1510 (C=C)

According to the above described procedure the following compounds can be prepared:

2-(4-hydroxyphenyl)-3-(quinolin-3-yl)acrylamide
$C_{18}H_{14}N_2O_2$ calc C 74.47 H 4.86 N 9.65 found C 74.32 H 4.71 N.9.51
MS m/z: 290
IR $cm^{-1}$ (KBr): 3450, 3320 (NH), 3500–2300 (OH), 1665(CONH), 1615, 1565, 1510, 1490 (C=C,C=N)
2-(4-hydroxyphenyl)-3-(naphth-1-yl)acrylamide;
2-(4-hydroxyphenyl)-3-(5,6,7,8-tetrahydronaphth-1-yl)acrylamide;
2-(4-hydroxyphenyl)-3-(5,6,7,8-tetrahydronaphth-2-yl)acrylamide;
2-(4-hydroxyphenyl)-3-(quinolin-2-yl)acrylamide; and
2-(4-hydroxyphenyl)-3-(quinolin-4-yl)acrylamide.

EXAMPLE 7

2-(d-hydroxyphenyl)-3-(napth-2-yl)acrylonitrile [I, Y=A, R=j, $R_2$=H, n=zero]

To a solution of 2-naphthaldehyde (156 mg, 1 mmol) and 4-hydroxybenzylcyanide (133 mg, 1 mmol) in dry ethanol (2 ml) is added portionwise under cooling sodium ethoxide (204 mg, 3 mmol) and the resulting solution is maintained for 96 h at room temperature. Then the solution is poured onto a mixture of ice and diluted hydrochloric acid. The precipitate formed is filtered off, washed with ice-cooled aqueous ethanol and dried in a vacuum-oven. Thus, pure title compound is obtained in 80% yield (217 mg).

$C_{19}H_{13}NO$ calc. C 84.11 H 4.83 N 5.16 found C 83.91 H 4.87 N 4.86

MS m/z: 271

IR cm$^{-1}$ (KBr) 3340 (OH), 2220 (CN), 1605, 1585, 1510 (C=C).

EXAMPLE 8

2-cyano-3-(1-hydroxy-5,6,7,8-tetrahydronaphth-2-yl)acrylamide [I, Y=B, R=a, $R_1$=$R_2$=H, $R_3$=$NH_2$, n=1]

The starting material for this de-etherification example is 2-cyano-3-(1-methoxy-5,6,7,8-tetrahydronaphth-2-yl)acrylamide, which can be obtained according to the procedure described in Example 1.

To a stirred solution of 2-cyano-3-(1-methoxy-5,6,7,8-tetrahydronaphth-2-yl)acrylamide (256 mg, 1 mmol) in anhydrous dichloromethane (10 ml) is added at −78° C. under nitrogen, over a period of 10 min, a 1.0M solution of boron tribromide in dichloromethane (3 ml, 3 mmol). The resulting mixture is stirred for another 1 h at −78° C. and then allowed to warm to room temperature. After stirring for 1.5 h at 20°–25° C. the mixture is cooled to −10° C. and then quenched by the dropwise addition of water (10 ml) over a 10-min period. After addition of ethylacetate (10 ml) the organic layer is separated, washed with water, dried with $Na_2SO_4$ and evaporated under vacuum to dryness. The residue is crystallized from ethanol thus giving 169 mg of pure title compound (yield 70%).

$C_{14}H_{14}N_2O$ calc. C 69.40 H 5.82 N 11.56 found C 69.30 H 5.85 N 11.41

MS m/z: 242

IR cm$^{-1}$ (KBr): 3500–3100 (NH,OH), 2210 (CN), 1685 ($CONH_2$), 1610, 1590, 1560

According to the above described procedure and starting from the corresponding phenolic methylether, the compounds mentioned in Examples 1, 2 and 3 can be obtained.

EXAMPLE 9

2-cyano-3-(1-acetoxy-5,6,7,8-tetrahydronaphth-2-yl) acrylamide [I-Y=B, R=a, $R_1$=$COCH_3$, $R_2$=H, $R_3$=$NH_2$, n=1]

The starting material for this acylation example is 2-cyano-3-(1-hydroxy-5,6,7,8-tetrahydronaphth-2-yl) acrylamide, which may be obtained according to the procedure described in example 1.

To a cooled solution of 2-cyano-3-(1-hydroxy-5,6,7,8-tetrahydronaphth-2-yl)acrylamide (242 mg, 1 mmol in dry pyridine (0.5 ml) is added acetic anhydride (204 mg, 2 mmol) and the mixture maintained at 0°–5° overnight. Thereupon the mixture is concentrated under vacuum, the residue dissolved in dichloromethane, the organic layer washed with water and then evaporated under reduced pressure. The crude product is crystallized from chloroform/methanol to yield pure title compound in 90% yield (256 mg).

$C_{16}H_{16}N_2O_3$ calc: C 67.59 H 5.67 N 9.85 found: C 67.41 H 5.45 N 9.71

MS m/z: 284

IR cm$^{-1}$ (KBr): 2300÷3200 (NH), 2200 (CN), 1750 ($CH_3COO$), 1690 ($CONH_2$), 1610, 1590, 1560

According to the above described procedure the phenols obtained in Examples 1 to 9 can be transformed into the corresponding $C_2$–$C_6$ alkanoyl derivatives.

EXAMPLE 10

Tablets each weighing 0.150 g and containing 25 mg of the active substance, can be manufactured as follows:

| composition (for 10000 tablets): | |
|---|---|
| 2-cyano-3-(1-hydroxynaphth-2-yl)acrylamide | 250 g |
| Lactose | 800 g |
| Corn starch | 415 g |
| Talc powder | 30 g |
| Magnesium stearate | 5 g |

The 2-cyano-3-(1-hydroxynaphth-2-yl)acrylamide, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

EXAMPLE 11

Capsules, each dosed at 0.200 g and containing 20 mg of the active substance can be prepared.

| Composition for 500 capsules: | |
|---|---|
| 2-cyano-3-(3-hydroxynaphth-2-yl)acrylamide | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

We claim:

1. A compound of the formula (I)

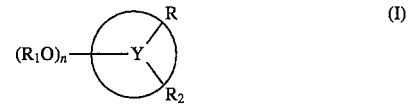

wherein

Y is a bicyclic ring system selected from the group consisting of (E), (F) and (G):

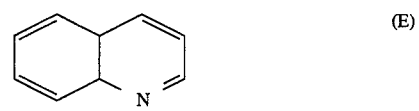

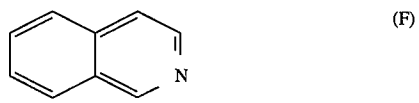

-continued (G)

[indole structure]

and R is a group of formula (e)

(e)

[oxindole methylene structure]

wherein
n is zero, 1 or 2;
$R_1$ is hydrogen, $C_1$–$C_6$ alkyl or $C_2$–$C_6$ alkanoyl; and
$R_2$ is hydrogen, halogen, cyano or $C_1$–$C_6$ alkyl;
or a pharmaceutically acceptable salt thereof; and wherein each of the substituents R, $OR_1$ and $R_2$ may be independently on either the aryl or the heteroaryl moiety of the bicyclic ring systems (E), (F) and (G); when (Y) is said ring system (G), R is linked to position 3 of the indole ring (G), and n is zero, then $R_2$ is not bromine linked to position 2 of the indole ring (G); and when (Y) is a ring system (G), R is linked to position 2 or 3 of the indole ring (G) and n is zero, then $R_2$ is not hydrogen.

2. A compound or salt according to claim 1 wherein $R_1$ is hydrogen, $C_1$–$C_4$ alkyl or $C_2$–$C_4$ alkanoyl; and $R_2$ is hydrogen.

3. A compound or salt according to claim 1, wherein (Y) is a bicyclic ring system (E)

[quinoline structure]

and $R_1$ and $R_2$ are hydrogen.

4. A compound selected from the group consisting of:
3-[(quinolin-5-yl) methylene]-2-oxindole;
3-[(6-hydroxyquinolin-5-yl) methylene]-2-oxindole;
3-[(7-hydroxyquinolin-5-yl) methylene]-2-oxindole;
3-[(8-hydroxyquinolin-5-yl) methylene]-2-oxindole;
3-[(quinolin-6-yl) methylene]-2-oxindole;
3-[(5-hydroxyquinolin-6-yl) methylene]-2-oxindole;
3-[(7-hydroxyquinolin-6-yl) methylene]-2-oxindole;
3-[(8-hydroxyquinolin-6-yl) methylene]-2-oxindole;
3-[(quinolin-2-yl) methylene]-2-oxindole;
3-[(4-hydroxyquinolin-2-yl) methylene]-2-oxinidole;
3-[(quinolin-4-yl) methylene]-2-oxindole; and
3-[(quinolin-3-yl) methylene]-2-oxindole;
or a pharmaceutically acceptable salt thereof;
wherein said compound, when appropriate, may be either Z- or E-diastereoisomers or Z, E-mixtures of said diasteroisomers.

5. A pharmaceutical composition comprising a pharmaceutically suitable carrier or diluent and a therapeutically effective amount of a compound of formula (I)

$$(R_1O)_n - Y\begin{array}{c}R\\R_2\end{array}$$  (I)

wherein

Y is a bicyclic ring system selected from the group consisting of (E), (F) and (G):

(E)

[quinoline structure]

(F)

[isoquinoline structure]

(G)

[indole structure]

and R is a group of formula (e)

(e)

[oxindole methylene structure]

wherein
n is zero, 1 or 2;
$R_1$ is hydrogen, $C_1$–$C_6$ alkyl or $C_2$–$C_6$ alkanoyl; and
$R_2$ is hydrogen, halogen, cyano or $C_1$–$C_6$ alkyl;
or a pharmaceutically acceptable salt thereof; and wherein each of the substituents R, $OR_1$ and $R_2$ may be independently on either the aryl or the heteroaryl moiety of the bicyclic ring systems (E), (F) and (G); when (Y) is said ring system (G), R is linked to position 3 of the indole ring (G), and n is zero, then $R_2$ is not bromine linked to position 2 of the indole ring (G); and when (Y) is a ring system (G), R is linked to position 2 or 3 of the indole ring (G) and n is zero, then $R_2$ is not hydrogen.

6. A method of treating a patient in need of a tyrosine kinase inhibitor, comprising the step of:
administering to said patient, in an amount effective to inhibit tyrosine kinase, a compound of formula (I)

$$Y\begin{array}{c}R\\(OR_1)_n\\R_2\end{array}$$  (I)

wherein

Y is a bicyclic ring system selected from the group consisting of (E), (F) and (G):

(E)

[quinoline structure]

(F)

[isoquinoline structure]

(G)

[indole structure]

and R is a group of formula (e)

(e) 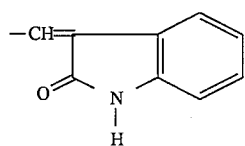
n is zero, 1 or 2;
$R_1$ is hydrogen, $C_1$–$C_6$ alkyl or $C_2$–$C_{61}$ alkanoyl;
or a pharmaceutically acceptable salt thereof; and wherein each of the substituents R, $OR_1$ and $R_2$ may be on either the aryl or the heteroaryl moiety of the bicyclic ring systems (E), (F) and (G).
* * * * *

UNITED STATES PATENT AND TRADEMARK OFFICE
CERTIFICATE OF CORRECTION

PATENT NO. : 5,488,057
DATED : Jan. 30, 1996
INVENTOR(S) : Franco Buzzetti, et al.

It is certified that error appears in the above-indentified patent and that said Letters Patent is hereby corrected as shown below:

On the title page, item [62], Related U.S. Application Data should read:

[62] Division of Ser. No. 126,687, Sep. 27, 1993, Pat. No. 5,374,652, which is a continuation of Ser. No. 768,259, Oct. 28, 1991, abandoned, which was filed as International Application No. PCT/EP31/00350 on Feb. 26, 1991.

Signed and Sealed this

Twenty-fourth Day of September, 1996

Attest:

BRUCE LEHMAN

Attesting Officer     Commissioner of Patents and Trademarks